United States Patent [19]

Dozzi et al.

[11] 4,325,885

[45] Apr. 20, 1982

[54] METHOD FOR PREPARATION OF OLIGOMERIC IMINIC DERIVATIVES OF ALUMINUM

[75] Inventors: Giovanni Dozzi, Milan; Salvatore Cucinella; Tito Salvatori, both of San Donato Milanese, all of Italy

[73] Assignee: Anic S.p.A., Palermo, Italy

[21] Appl. No.: 149,896

[22] Filed: May 15, 1980

Related U.S. Application Data

[62] Division of Ser. No. 20,837, Mar. 15, 1979, Pat. No. 4,239,692.

[30] Foreign Application Priority Data

Apr. 12, 1978 [IT] Italy ............................. 22221 A/78

[51] Int. Cl.$^3$ ............................................. C07F 5/06
[52] U.S. Cl. ............................................... 260/448 R
[58] Field of Search .................................... 260/448 R

[56] References Cited

U.S. PATENT DOCUMENTS

| | | | |
|---|---|---|---|
| 3,983,150 | 9/1976 | Casensky et al. | 260/448 R |
| 4,022,809 | 5/1977 | Cucinella et al. | 260/448 R |
| 4,032,553 | 6/1977 | Dozzi et al. | 260/448 R |
| 4,064,153 | 12/1977 | Cucinella et al. | 260/448 R |
| 4,122,108 | 10/1978 | Cucinella et al. | 260/448 R |
| 4,128,566 | 12/1978 | Corbellini et al. | 260/448 R |
| 4,128,567 | 12/1978 | Corbellini et al. | 260/448 R |

*Primary Examiner*—Helen M. S. Sneed
*Attorney, Agent, or Firm*—Morgan, Finnegan, Pine, Foley & Lee

[57] ABSTRACT

There are disclosed oligomeric aluminum hydride iminic derivatives, to be employed as catalysts in polymerization processes and which are prepared by causing alkali-metal or alkaline-earth-metal alanates to react with a primary amine which contains a group of the type $-X-R''_m$, wherein X is a nitrogen atom or an oxygen atom and m is equal to the valence of X minus one. The compounds have a trimeric or a tetrameric "open cage" spatial configuration.

5 Claims, No Drawings

METHOD FOR PREPARATION OF OLIGOMERIC IMINIC DERIVATIVES OF ALUMINUM

This is a division, of application Ser. No. 20,837 filed Mar. 15, 1979 now U.S. Pat. No. 4,239,692.

This invention relates to oligomeric iminic derivatives of aluminum hydride and to methods for their preparation.

More particularly, it is an object of the present invention to provide a novel class of oligomeric iminoalanes corresponding to the formula:

$$[(HAlN-R'-XR''_m)_i(H_2AlNH-R'-XR''_m)_j] \quad (I)$$

wherein
1. R' is (i) a linear aliphatic bivalent hydrocarbon radical, or a branched radical, which may be aryl-substituted, having from 1 to 20 carbon atoms,
   (ii) a cycloaliphatic bivalent hydrocarbon radical, which may be alkyl- or aryl-substituted and (iii) an aromatic bivalent radical, which may also be alkyl-substituted, having from 1 to 20 carbon atoms;
2. X is a nitrogen atom or an oxygen atom;
3. R'' indicates (1) is (i) a linear or branched hydrocarbon radical, which may also be aryl-substituted, having from 1 to 20 carbon atoms, (ii) a cycloaliphatic hydrocarbon radical, which may also be alkyl- or aryl-substituted having from 1 to 20 carbon atoms, (iii) an aromatic radical, which may also be alkyl-substituted, having from 1 to 20 carbon atoms;
4. m is a function of the nature of X and is equal to v-1, v being the valence of X, and where m is greater than 1, the radicals R'' can be equal to or different from each other,
5. i+j equals z which is an integer comprised between 4 and 20. In addition, i can be equal to or different from j.

The known literature describes a number of methods for the synthesis of iminoderivatives of aluminum hydride of the oligomeric type, which are also called poly-(N-alkyliminoalanes).

More particularly, the Assignee of this application is also the owner of a number of patent applications in this field.

The assignee has, in fact, disclosed methods for
(1) the preparation of N-alkyliminoalanes of the oligomeric type having the formula $$(HAlNR)_n \quad (II)$$

wherein R is an aliphatic hydrocarbon radical, or an aromatic or cycloaliphatic radical, and n is an integer which is equal to or smaller than 10.

These compounds are characterized by tridimensional "closed cage" structures which are derived from the condensation of 4-membered rings $(HAlNR)_2$ (III) and/or 6-membered rings $(HAlNR)_3$ (IV) as disclosed in U.S. Pat. No. 4,064,153.

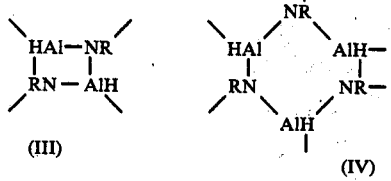

Examples of such are the following structures (V) and (VI), tetrameric $(HAlNR)_4$ and hexameric $(HAlNR)_6$, respectively.

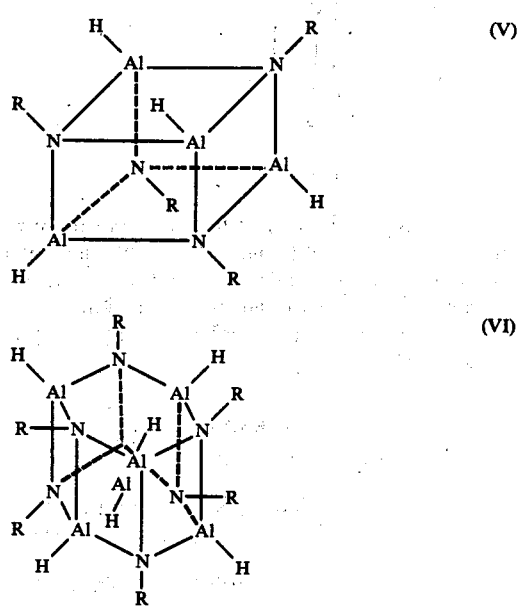

The Assignee has also disclosed methods for the proportion of N-oligomeric N-alkyliminoalanes having the formulas:

$$(HAlNR)_x(H_2AlNHR) \quad (VII)$$

wherein R is an aliphatic, aromatic or cycloaliphatic hydrocarbon radical and the sum x+y is equal to n which is an integer equal to or smaller than 10.

Such compounds are characterized by tridimensional "open cage" molecular structures which are derived from the condensation of the aforementioned rings (III) or (IV), having 4 or 6 members respectively, with aminic units $>H_2Al-NHR<$ (VIII) and/or with 4-membered and/or 6-membered rings of the types (IX) or (X). These compounds are:

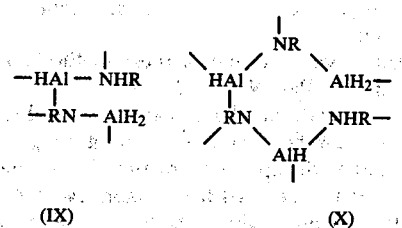

have been disclosed, among other iminic derivatives of aluminum, in the U.S. Pat. No. 4,032,553.

Examples of such compounds are the tetramer (XI) and the hexamer (XII)

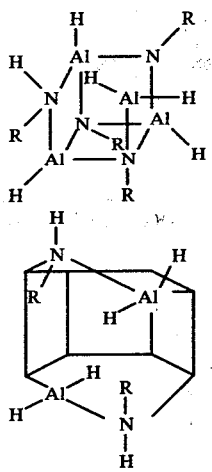

According to the U.S. Patents aforementioned, compounds of the type (II) and (VII) are obtained by reacting complexes of aluminum hydride with primary amines (reaction a), or alanates of alkali metal- or alkaline earth metals with hydrohalides of primary amines (reaction b):

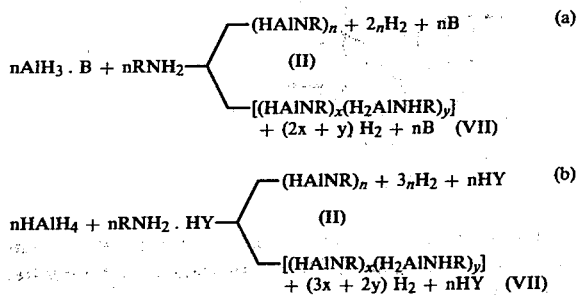

wherein:
B = is a Lewis base, such as ether, a tertiary amine, tetrahydrofuran and the like, n, x and y have the values indicated above, M is Li, Na, K and like including ½Mg, ½Ca and the like and Y is a halogen.

The reactions discussed above lead to the formation of "closed cage" structures (II) or of "open-cage" structures (VII) depending upon the conditions of the reaction.

For example, the adoption of moderate reaction temperatures (generally below 40° C.) encourages the formation of compounds having an "open-cage" structure.

The same Assignee has also disclosed two further methods for the preparation of poly(N-alkyliminoalanes) which imply the use of metallic aluminum as the starting product.

In accordance with the first of these methods in accordance with U.S. Pat. No., 4,022,809 the alanate of an alkali- or an alkaline earth metal reacts with a primary amine (reaction c) to give poly(N-alkyliminoalane) with separation of the alkali-metal or the alkaline earth-metal hydride, which can be converted into the alanate again by reaction with metallic aluminum (reaction d) so that the result of the combination of the two reactions is equivalent to the synthesis of poly(N-alkyliminoalane) starting from aluminum and hydrogen (reaction e):

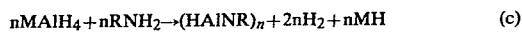

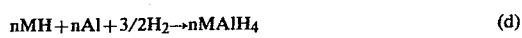

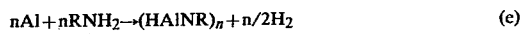

The direct synthesis of poly(N-alkyliminoalanes) in a single step, consistent with reaction (e), has also been achieved by the Assignee by using, for example, small amounts of MAlH$_4$ as an activator (U.S. patent appln. No. 601,209 filed on Aug. 1, 1975), abandoned.

At any rate, by using primary amines RNH$_2$, wherein R is an alkyl-, aryl-, or cycloalkyl hydrocarbon radical, the resulting products of reactions (c) and (d) are products having a "closed cage" structure of the type (II).

The practical applications of the N-alkyliminoalanes and of a few derivatives thereof have been thoroughly studied (see S. Cucinella, Chim. Ind. (Milan) 59, 696, (1977).

From the study of such practical applications, it has been determined that chemical or structural modifications of the poly(N-alkyliminoalanes) involve pronounced variations in their activity. For example, in the case of polymerization of isoprene with binary systems poly(N-alkyliminoalanes)-TiCl$_4$, when employing poly(N-alkyliminoalanes) having a hydride hydrogen-to-aluminum ratio higher than 1, a higher yield of 1,4-cis-polyisoprene has been obtained as compared with yields obtained when using poly(N-alkyliminoalanes) having a hydride hydrogen-to-aluminum ratio equal to 1. (A. Balducci, M. Bruzzone, S. Cucinella, A. Mazzei, Rubber Chem. Technol., 48, 736 (1975).

It is thus apparent, inter alia, how important are those syntheses which permit the formation of poly(N-alkyliminoalanes) having an "open-cage" structure, which have a content of hydride hydrogen higher (H$_{active}$/Al greater than 1) in comparison to those of the corresponding "closed-cage" compounds (H$_{active}$/Al = 1).

In this respect, the requirement or need of a further advance in the synthesis of poly(N-alkyliminoalanes) in respect to arriving at compounds with an "open cage" structure by a simple method, which had to be different from the expensive procedures based on the reactions a and b above which involve the loss of hydride hydrogen and the separation and the loss of alkali metals or of alkaline-earth metals.

It is emphasized that, as far as the present knowledge suggests, methods described in the reactions (c) and (d) starting from different primary amines RNH$_2$, wherein is R an alkyl, an aryl or a cycloalkyl group, have, in any case, furnished poly(N-alkyliminoalanes) of type (II), that is a "closed cage" tridimensional structure.

It has now been found, and is the subject matter in accordance with the present invention, that it is possible to obtain, in quite a simple and unexpensive manner, poly(N-alkyliminoalanes) having an "open cage" structure, either starting from alanates of alkali metals of alkaline earth metals and an amine, on starting from metallic aluminum and an amine.

The essential condition for carrying out the novel syntheses in accordance with this invention is that the starting primary amine contain in its chain a group of the type —X—R''$_m$ wherein the symbols have the same meanings as indicated above. These syntheses are effected according to the reactions (f) and (g) below.

(f)
$$zMAlH_4 + zH_2N-R'-XR''_m \rightarrow [(HAlN-R'-XR''_m)_i(H_2AlNH-R'-XR''_m)_j] + zMH + (2i+j)H_2 \quad (I)$$

wherein

M is Li, Na, K and the like or (Mg/2, Ca/2; and z is i+j (g)
$$zAl + zH_2N-R'-XR''_m \rightarrow ](HAlN-R'-XR''_m)_i(H_2AlNH-R'-XR''_m)_j] + qH_2 \quad (I)$$

wherein q = (i/2)−(j/2)

The products which are obtained from these syntheses are, as outlined above, compounds having an "open cage" tridimensional structure which provide considerable contribution towards improved activity, for example, in polymerization runs.

The reactions can be conducted in hydrocarbon and ethereal solvents, at a temperature comprised between 0° C. and the temperature of decomposition of the product.

More particularly, it is preferred, for reaction (f), to operate at the boiling point of the solvent and it is also preferred that an excess of MAlH$_4$ be employed.

For reaction (g), the preferred temperature range is from 90° C. to 150° C. In the latter case, it is necessary to work under a hydrogen atmosphere and, preferably, in the presence of an activator.

The hydrogen pressure may vary from 1 to 1000 kg/cm² and is preferably maintained between 100 and 200 kg/cm².

The activator is selected from among alkali metals and their hydrides, alkaline-earth metals and their hydrides, alanates of alkali metals and alkaline earth metals, alkyl- or amide derivatives of metals of the 2nd and the 3rd Group, for example, magnesium- or aluminum-alkyls, derivatives of aluminum hydride or, more particularly, the reaction product itself.

Preferably, the activator is employed in a quantity which is equal to, or lower than molar percent relative to the amine.

It is also preferred to use an excess of aluminum. In the case of a strong excess, the latter can also be used for subsequent syntheses without any further addition of activators.

As a rule, when subjected to a long heating time, "open cage" structures of the type (I) are converted into the corresponding "closed cage" structures according to the reaction (h) and this is another aspect of the present invention.

$$[(HAlN-R'-XR''_m)]_i (H_2AlNH-R'-XR''_m)_j \xrightarrow{(h)}$$

(I)

$$(HAlN-R'-XR''_m)_z + jH_2$$

(XIII)

Such a conversion can also be achieved by subjecting the reaction mixture of (f) or of (g), which contains the product (I) without the separation of the latter to prolong heating.

The novel imino derivatives of the types (I) and (XIII) are capable of complexing the Lewis bases.

They are, moreover, potential complexing agents for other hydride molecules which exhibit the character of Lewis acids, such as hydrides of the metals of the 3rd Group MH$_3$(M = B, Al, Ga and the like) or their derivatives by the formation of bonds $$\begin{array}{c} -X\,R''_m \\ \downarrow \\ MH_3 \end{array}$$

which are made possible by the basic nature of X.

The atoms of hydride hydrogen can be either partially or entirely substituted by other ligands such as alkyl, halogen and alcoxy group by the reactions which are known for the poly(N-alkyliminoalanes) (see S. Cucinella, Chim. Ind. (Milan) 59, 696 (1977).

The novel imino derivatives and their complexes with Lewis bases or hydride or alkyl derivatives of other metals can be employed with advantage:

(a) as stoichiometric reactants for the hydrogenation of organic functions;
(b) as compounds of hydrogenation catalytic systems, in union with derivatives of transition metals;
(c) as polymerization catalysts, either alone or in union with derivatives of transition metals, for the polymerization or the copolymerization of mono-olefins, diolefins and functional unsaturated monomers.

EXAMPLE 1

Working under a nitrogen atmosphere in a 250 ml flask, there are introduced 2.51 grams (68 millimols) of LiAlH$_4$ slurried in 100 mls of toluene. Through a dropping funnel there are added 40 millimols of 1-dimethylamine-2-propylamine in 50 mls of toluene.

The reaction mixture is then stirred at the reflux temperature of the solvent until the ratio N/Al in the solution is about 2. Eventually, the solution is filtered, the toluene solution is evaporated under reduced pressures and the residue which is obtained is dried in a vacuum, weighed (4.2 grams) and analyzed.

Found: Al = 20.9%; N = 20.8%; active H = 11.30 milliequiv./g corresponding to N/Al = 1.92 and H active/Al = 1.46.

The analyses indicate the formation of an oligomeric open structure having a composition which is nearly:

$$\{[HAlNCH(CH_3)CH_2N(CH_3)_2]_2[H_2AlNHCH(CH_3)CH_2N(CH_3)_2]\}_2 \quad (XVI)$$

and for which the calculations were:

Al = 20.9%; N = 21.7%; H$_{active}$ = 11.62 milliequivalents/g.

The formation of an "open cage" tetrameric structure corresponding to that indicated by the chemical analyses is corroborated by results of the physicochemical investigations.

As a matter of fact, the mass spectrum is dominated by ions which can be attributed to the tetramer [HAlNCH(CH$_3$)CH$_2$N(CH$_3$)$_2$]$_4$(M = 512) as formed from the corresponding "open cage" tetramer under the test conditions; ions at m/e = 511 are observed, corresponding to (M−H)+, and ions at m/e=454 deriving from the molecular ion by the loss of a radical —CH$_2$N(CH$_3$)$_2$.

Besides the dominating presence of the tetrameric structure, the mass spectrometric analysis also indicates small amounts of the pentamer.

The $^1$HNMR spectrum in benzene is in agreement with the formation of an "open cage" tetrameric structure having the composition (XVI) inasmuch as there are observed two singlets at $\tau$7.7 and at $\tau$7.5 with a relative intensity of nearly 1:1 which can be attributed to the geminal methyls N(CH$_3$)$_2$ of the groups: NCH(CH$_3$)CH$_2$N(CH$_3$)$_2$ and the groups NHCH(CH$_3$)CH$_2$N(CH$_3$)$_2$, respectively.

The I.R. spectrum is nujol exhibits a $\nu$Al-H band which is very broadened at about 1690 cm$^{-1}$.

EXAMPLE 2

A liter stainless steel autoclave, equipped with magnetic stirrer of the anchor type and which has previously been evacuated of air, is charged with powdered aluminum (160 millimols), NaAlH$_4$ (4 millimols), 1-dimethylamino-2-propylamine (90 millimols) in a total of 300 mls of toluene.

The autoclave is pressurized with hydrogen and the reaction mixture is stirred at 140° C. and under 160 kg/cm$^2$ from approximately 18 hours. Upon cooling and release of pressure, the autoclave is emptied of its contents. Filtration is carried out to separate the excess aluminum dust and the toluene solution is evaporated under reduced pressures. A product is obtained, which is vacuum dried and analyzed.

Found: Al=20.9%; N=20.6%; H$_{active}$=11.53 milliequivalents/g corresponding to N/Al=1.9 and H$_{active}$/Al=1.49. Calculated for: {[HAlNCH(CH$_3$)CH$_2$N(CH$_3$)$_2$]$_2$[H$_2$AlNHCH(CH$_3$)CH$_2$N(CH$_3$)$_2$]$_2$} Al=20.9%; N=21.7%; H$_{active}$=11.62 milliequivalents/g.

The yield is quantitative relative to the amine introduced in the reaction. The physico-chemical tests (mass-spectrometry, $^1$HNMR) confirm the formation of an open cage tetrameric structure on the basis of the results reported in Example 1. The IR spectrum in nujol exhibits a $\nu$Al-H band which is broadened somewhat with a peak at about 1650 cm$^{-1}$ and a shoulder at about 1750 cm$^{-1}$.

EXAMPLE 3

Using the same procedures and the same reactants as employed in Example 2 but diethyl ether instead of toluene and carrying out the reaction at 100° C. and 130 kg/cm$^2$, the present Example was carried out. On completion and with evaporation of the ethereal solution, a solid product is obtained which is dried under vacuum and analyzed.

Found: Al=21.3%; N=21.7%; H$_{active}$=10.40 milliequivalents/g Correspondingly: N/Al=1.97; H$_{active}$/Al=1.32. Calculated for {[HAlNCH(CH$_3$)CH$_2$N(CH$_3$)$_2$]$_3$[H$_2$AlNHCH(CH$_3$)CH$_2$N(CH$_3$)$_2$]} (XVII) Al=21.0%; N=21.8%; H$_{active}$=9.73 milliequivalents/g.

The yield is quantitative with respect to the amine introduced in the reaction. The same spectrometry is in agreement with the formation of a tetrameric structure, including traces of a pentameric structure.

The $^1$HNMR spectrum in benzene is in agreement with the formation of an "open cage" tetrameric structure having the composition (XVII). As a matter of fact there are observed two singlets at 96 7.7 and at 96 7.5 having a relative intensity of nearly 3:1 which can be attributed to the geminal methyls N(CH$_3$)$_2$ of the groups NCH(CH$_3$)CH$_2$N(CH$_3$)$_2$ and of the group: NHCH(CH$_3$)CH$_2$N(CH$_3$)$_2$.

The IR Spectrum in nujol exhibits an absorption band $\nu$Al-H which is broadened, with a maximum at about 1750 cm$^{-1}$ and a shoulder at about 1650 cm$^{-1}$.

EXAMPLE 4

A liter stainless steel autoclave equipped with an anchor-type magnetic stirrer, which has previously been evacuated of air, is charged with powdered aluminum (200 millimols), NaAlH$_4$ (5 millimols), 3-dimethylamino-1-propylamine (120 millimols) in a total volume of 250 mls of toluene. The autoclave is pressurized with hydrogen and the reaction mixture is stirred at 145° C. under 165 kg/cm$^2$ for 36 hours. Upon cooling the autoclave and releasing its internal pressure, the contents is recovered. By evaporating the reaction toluene solution under reduced pressures a solid product is obtained which is dried under vacuum and analyzed.

Found: Al=19.9%; N=19.8%; H$_{active}$=10.1 milliequivalents/g corresponding to: N/Al=1.92; H$_{active}$/Al=1.37 Calculated for: [HAlN—(CH$_2$)$_3$—N(CH$_3$)$_2$]$_4${[H$_2$AlNH—(CH$_2$)$_3$N(CH$_3$)$_2$]$_2$ Al=21.0%; N=21.8%; H$_{active}$=10.36 milliequivalents/g.

The reaction solution contains about 30% of the as-formed product and the remainder is recovered in the solid state together with the excess powdered aluminum and from which it can be separated by extraction with toluene. The physico-chemical tests indicate that a hexamer predominates. As a matter of fact, the mass spectrum is dominated by ions which can be ascribed to the hexamer [HAlN—(CH$_2$)$_3$—N(CH$_3$)$_2$]$_6$ (M=768) as formed from the corresponding "open cage" hexamer under the test conditions. More exactly, there are observed, in addition to the molecular ion at m/e 768, ions at m/e 767 corresponding to (M-H)+ $^{and\ at\ m/e}$ 710 derived from the molecular ion by loss of a —CH$_2$N(CH$_3$)$_2$ radical.

Besides the prevailing presence of the hexameric structure, the mass spectrometry indicates also the formation of traces of a heptamer. The IR-spectrum in nujol exhibits a $\nu$Al-H absorption band which is broadened with a peak at about 1780 cm$^{-1}$.

EXAMPLE 5

The present Example shows how, by heating, the open tetramer: {[HAlNCH(CH$_3$)CH$_2$N(CH$_3$)$_2$]$_2$[H$_2$AlNHCH(CH$_3$)CH$_2$N(CH$_3$)$_2$]$_2$} described in Example 2 hereof is converted into the corresponding closed tetramer:

[HAlNCH(CH$_3$)CH$_2$N(CH$_3$)$_2$]$_4$ 2 grams of the compound described in Example 2 are dissolved in about 50 mls of toluene and the solution is refluxed for about 6 hours. The solution is filtered to have it limpid and is evaporated under reduced pressures and the as-obtained product is dried under vacuum and analyzed.

Found: Al=19.8%; N=19.9%; H$_{active}$=7.7 milliequivalents/g corresponding to: N/Al=1.94; H$_{active}$/Al=1.05 Calculated for: [HAlNCH(CH$_3$)CH$_2$N(CH$_3$)$_2$]$_4$ Al=21.1%; N=21.9%; H$_{active}$=7.8 milliequivalents/g.

Consistently with the formation of a "closed cage" structure, the $^1$HNMR spectrum in benzene shows a single broad signal for which the geminal methyls —N(CH$_3$)$_2$ at $\tau 7.7$ are responsible. The IR-spectrum in nujol displays an absorption band $\nu$Al-H with a definite peak at 1750 cm$^{-1}$. Mass spectrometry confirms the formation of a tetrameric structure (m/e=511; 454).

We claim:

1. A process for the preparation of oligomeric derivatives of aluminum having a tridimensional "open cage" structure of the formula: [(HAlN—R'—XR"$_m$)$_i$(H$_2$AlNH—R'—XR"$_m$)$_j$] wherein:
   (a) R' is (i) a linear, branched or aryl-substituted bivalent hydrocarbon aliphatic radical having from 1 to 20 carbon atoms, (ii) a bivalent cycloaliphatic radical or alkyl- or arylsubstituted bivalent cycloaliphatic radical or (iii) an aromatic or alkylsubstituted aromatic bivalent radical having from 1 to 20 carbon atoms,
   (b) X is a nitrogen or an oxygen atom,
   (c) R" is (i) a linear branched or aryl-substituted aliphatic hydrocarbon radical having from 1 to 20 carbon atoms, (ii) a cycloaliphatic hydrocarbon radical or alkyl or arylsubstituted hydrocarbon radical having from 1 to 20 carbon atoms, or (iii) an aromatic or alkylsubstituted aromatic radical having from 1 to 20 carbon atoms,
   (d) m is a function of the nature of X and is equal to v-1, v being the valence of X and wherein m is greater than 1 the radicals R" can be equal to, or different from, each other,
   (e) i+j equals z, z being an integer between 4 and 20 and in addition i can be equal to j or different from j comprising the steps of reacting at a temperature between 0° C. and the decomposition temperature of the reaction product and at a hydrogen pressure of from 1-100 kg/cm$^2$ metallic aluminum and an amine, wherein said amine is a primary amine containing at least one group of the type —X—R"$_m$— wherein X, R" and m are as defined above and obtaining oligomeric derivatives having said tridimensional "open cage" structure.

2. A process according to claim 1 wherein the reaction is carried out in the presence of a solvent selected from the group consisting of hydrocarbonaceous solvents and ethereal solvents.

3. A process according to claim 1 the reaction is carried out at a temperature between 90° C. and 150° C.

4. A process according to claim 1 wherein the reaction is carried out at a hydrogen pressure between 100 and 200 kg/cm$^2$.

5. A process according to claim 1 wherein the reaction is carried out in the presence of an activator selected from the group consisting of alkali metals, alkaline earth metals and their hydrides, alanates of alkali metals and alkaline earth metals, an alkyl or imine derivative of the metals of the 2nd and 3rd Groups of the Periodic Table, a derivative of aluminum hydride and the reaction product itself, said activator being employed in an amount equal to or lower than 5 molar percent relative to the amine.

* * * * *